United States Patent
Saeki et al.

(10) Patent No.: US 10,010,265 B2
(45) Date of Patent: Jul. 3, 2018

(54) METHOD OF PRODUCING TEMPERATURE SENSOR, AND TEMPERATURE SENSOR

(71) Applicant: NIHON KOHDEN CORPORATION, Tokyo (JP)

(72) Inventors: Kota Saeki, Tokyo (JP); Masayuki Inoue, Tokyo (JP); Katsumi Nakaichi, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 310 days.

(21) Appl. No.: 14/718,737

(22) Filed: May 21, 2015

(65) Prior Publication Data

US 2015/0342502 A1 Dec. 3, 2015

(30) Foreign Application Priority Data

Jun. 2, 2014 (JP) ................. 2014-114169

(51) Int. Cl.
| | |
|---|---|
| *A61B 5/08* | (2006.01) |
| *A61B 5/087* | (2006.01) |
| *A61M 16/00* | (2006.01) |
| *A61M 16/06* | (2006.01) |
| *A61M 16/08* | (2006.01) |
| *G01K 1/10* | (2006.01) |

(Continued)

(52) U.S. Cl.
CPC ....... *A61B 5/0878* (2013.01); *A61M 16/0003* (2014.02); *A61M 16/0666* (2013.01); *A61M 16/0841* (2014.02); *G01K 1/10* (2013.01); *G01K 13/002* (2013.01); *G01K 13/02* (2013.01); *A61B 2562/0276* (2013.01); *A61B 2562/12* (2013.01); *A61M 2230/50* (2013.01); *G01K 2013/024* (2013.01); *Y10T 29/49087* (2015.01)

(58) Field of Classification Search
CPC ............... A61B 5/0878; G01K 13/002; G01K 2013/024
See application file for complete search history.

(56) References Cited

U.S. PATENT DOCUMENTS

| | | | |
|---|---|---|---|
| 3,884,219 A | 5/1975 | Richardson et al. | |
| 2005/0096558 A1 | 5/2005 | Friedman et al. | |
| 2014/0066800 A1 | 3/2014 | Takatori et al. | |

FOREIGN PATENT DOCUMENTS

| | | |
|---|---|---|
| EP | 2702942 A1 | 3/2014 |
| GB | 1518521 A | 7/1978 |
| JP | S49-128590 A | 12/1974 |

(Continued)

OTHER PUBLICATIONS

Machine Translation of JP2013-149807A. Publication date Aug. 1, 2013.*

(Continued)

*Primary Examiner* — Christian Jang
(74) *Attorney, Agent, or Firm* — Pearne & Gordon LLP (57) ABSTRACT

A method of producing a temperature sensor which is configured to detect a temperature change of a respiratory gas of a subject, includes: preparing a rod-like heat sensitive element which includes a heat sensitive portion in a tip end portion; placing the heat sensitive portion in a cavity of a mold; injecting a resin material into the cavity to mold a protective portion which covers the heat sensitive element; and releasing the tip end portion in which the protective portion is formed, from the mold.

11 Claims, 6 Drawing Sheets

(51) Int. Cl.
   *G01K 13/00* (2006.01)
   *G01K 13/02* (2006.01)

(56) References Cited

FOREIGN PATENT DOCUMENTS

| | | |
|---|---|---|
| JP | S59-191629 U1 | 12/1984 |
| JP | S60-210729 A | 10/1985 |
| JP | S62-057564 A | 3/1987 |
| JP | S64-046007 U1 | 3/1989 |
| JP | H06-304962 A | 11/1994 |
| JP | H09-051950 A | 2/1997 |
| JP | 2005-019644 A | 1/2005 |
| JP | 2005-263189 A | 9/2005 |
| JP | 2013-149807 A | 8/2013 |
| JP | 2014-064881 A | 4/2014 |

OTHER PUBLICATIONS

Nihon Kohden Corporation; "Sensor for Analyzing Sleep Air Flow Sensor (Adult Size) TR-101A"; produced on Feb. 23, 2011, revised on Jun. 14, 2013. Internet URL: http://www.nihonkohden.co.jp/iryo/documents/pdf/H902599A.pdf; searched on Jun. 2, 2014.
Sep. 29, 2015 Extended European Search Report issued in European Patent Application No. 15169162.3.
European Office Action issued in Patent Application No. EP 15 169 162.3 dated Nov. 6, 2017.
Japanese Office Action issued in Patent Application No. JP-2014-114169 dated Oct. 3, 2017.
Japanese Office action issued in Patent Application No. JP-2014-114169 dated May 8, 2018.

\* cited by examiner

METHOD OF PRODUCING TEMPERATURE SENSOR, AND TEMPERATURE SENSOR

CROSS-REFERENCE TO RELATED APPLICATION(S)

This application is based upon and claims the benefit of priority from prior Japanese patent application No. 2014-114169, filed on Jun. 2, 2014, the entire contents of which are incorporated herein by reference.

BACKGROUND

The presently disclosed subject matter relates to a method of producing a temperature sensor which detects a temperature change of the respiratory gas of the subject, and also to a temperature sensor which detects a temperature change of the respiratory gas of the subject.

As a temperature sensor of this kind, there is a sensor attachable to a member having a gas passage through which the respiratory gas of the subject is to be passed. For example, a temperature sensor disclosed in Non-patent Literature 1 includes a plurality of rod-like heat sensitive elements. A heat sensitive portion is disposed in a tip end portion of each of the rod-like heat sensitive elements. The heat sensitive portions are placed so as to be opposed respectively to the nostrils and mouth of the subject, and configured so as to detect a temperature change of the respiratory gas of the subject.

(Non-patent Literature 1) Merchandise catalog entitled "Sensor for analyzing sleep Air flow sensor (adult size) TR-101A", produced on Feb. 23, 2011, revised on Jun. 14, 2013, Nihon Kohden Corporation, (Searched on Jun. 2, 2014), Internet <URL: http://www.nihonkohden.co.jp/iryo/documents/pdf/H902599A.pdf>

The tip end portions of the heat sensitive elements are coated by a resin in order to protect the respective heat sensitive portions. The resin coating process is performed in a step called dipping. Specifically, the tip end portions of the heat sensitive elements are immersed in a resin bath, and then lifted up, and the resin adhering to the tip end portions is solidified.

SUMMARY

The presently disclosed subject matter may provide a technique to produce a plurality of temperature sensors having constant characteristics, more efficiently, at a lower cost, and more stably.

There may be provided a method of producing a temperature sensor which is configured to detect a temperature change of a respiratory gas of a subject, the method comprising: preparing a rod-like heat sensitive element which includes a heat sensitive portion in a tip end portion; placing the heat sensitive portion in a cavity of a mold; injecting a resin material into the cavity to mold a protective portion which covers the heat sensitive element; and releasing the tip end portion in which the protective portion is formed, from the mold.

The heat sensitive portion may be one of a junction of a pair of metal wires constituting a thermocouple, a thermistor, and a resistance temperature detector, and the resin material may be injected into the cavity along a longitudinal direction of the heat sensitive element.

The heat sensitive portion may include a plurality of wire members, the heat sensitive element may include a cylindrical member which is configured to bundle the plurality of wire members, and, when the tip end portion is placed in the cavity, a tip end edge of the cylindrical member may be placed in the cavity.

In a portion defining the cavity, a parting surface of the mold may extend in parallel to a longitudinal direction of the heat sensitive element.

There may be also provided a temperature sensor which is configured to detect a temperature change of a respiratory gas of a subject, the temperature sensor comprising: a rod-like heat sensitive element which includes a heat sensitive portion in a tip end portion; and a resin-made protective portion which covers the heat sensitive element, and in which a line trace is formed.

The heat sensitive portion may be one of a junction of a pair of metal wires constituting a thermocouple, a thermistor, and a resistance temperature detector, and a cut trace may be formed in a tip end of the protective portion.

The heat sensitive portion may include a plurality of wire members, the rod-like heat sensitive element may include a cylindrical member which is configured to bundle the plurality of wire members, and a tip end edge of the cylindrical member may be covered by the protective portion.

The line trace may extend in a plane which is parallel to a longitudinal direction of the heat sensitive element.

The sensor may include a connecting portion that is attachable to a member including a gas passage through which the respiratory gas of the subject is to be passed.

DETAILED DESCRIPTION OF EXEMPLARY EMBODIMENTS

Hereinafter, an embodiment will be described in detail with reference to the accompanying drawings. In the figures, the scale is adequately changed in order to draw components in a recognizable size.

Figure 1A:
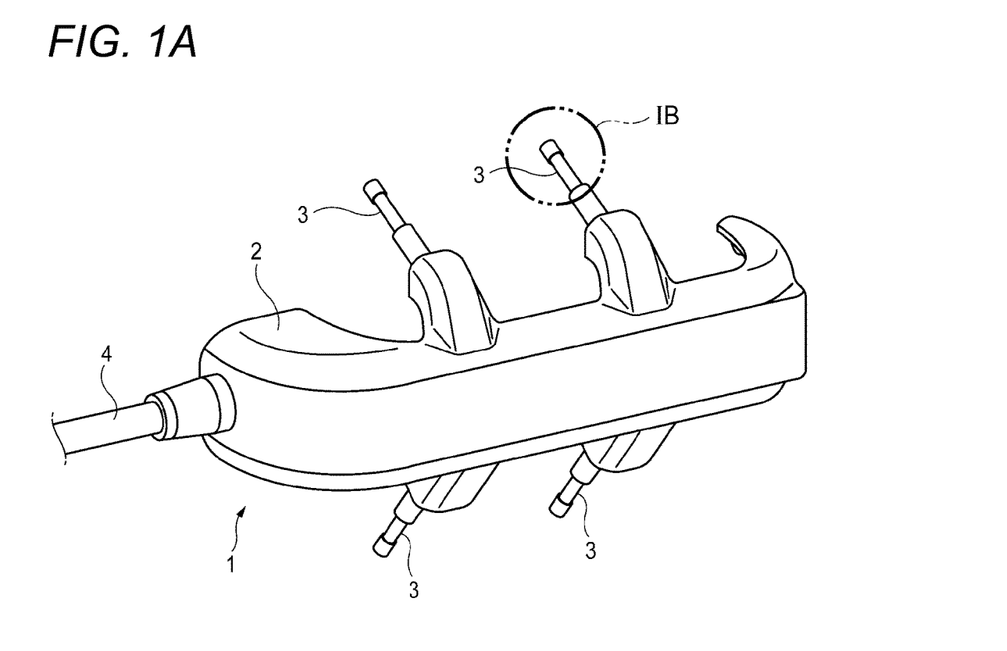
FIGS. 1A and 1B are views showing the appearance of a temperature sensor of an embodiment.

FIG. 1A is a perspective view showing the appearance of a temperature sensor 1 of an embodiment. The temperature sensor 1 includes a plurality of heat sensitive elements 3 which are supported by the body unit 2, and a cable 4.

Figure 1B:
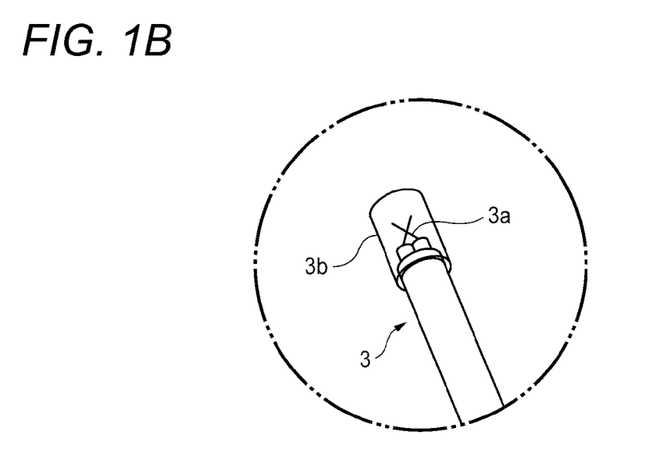

FIG. 1B enlargedly shows the portion enclosed by the circle IB in FIG. 1A. Each of the heat sensitive elements 3 has a rod-like appearance. A heat sensitive portion 3a is attached to a tip end portion of each heat sensitive element 3. In the embodiment, the heat sensitive portion 3a is configured by a junction of a pair of metal wires constituting a thermocouple. The heat sensitive portion 3a is covered by a resin-made protective portion 3b.

The heat sensitive elements 3 are electrically connected to the cable 4 in the body unit 2. The heat sensitive elements 3 are configured so as to output an electric signal corresponding to a detected temperature. The cable 4 is configured so as to transmit the electric signals from the heat sensitive elements 3 to an eternal apparatus which is not shown.

Referring to FIGS. 2A to 4, a method of producing the heat sensitive elements 3 which constitute apart of the temperature sensor 1 will be described.

Figure 2A:
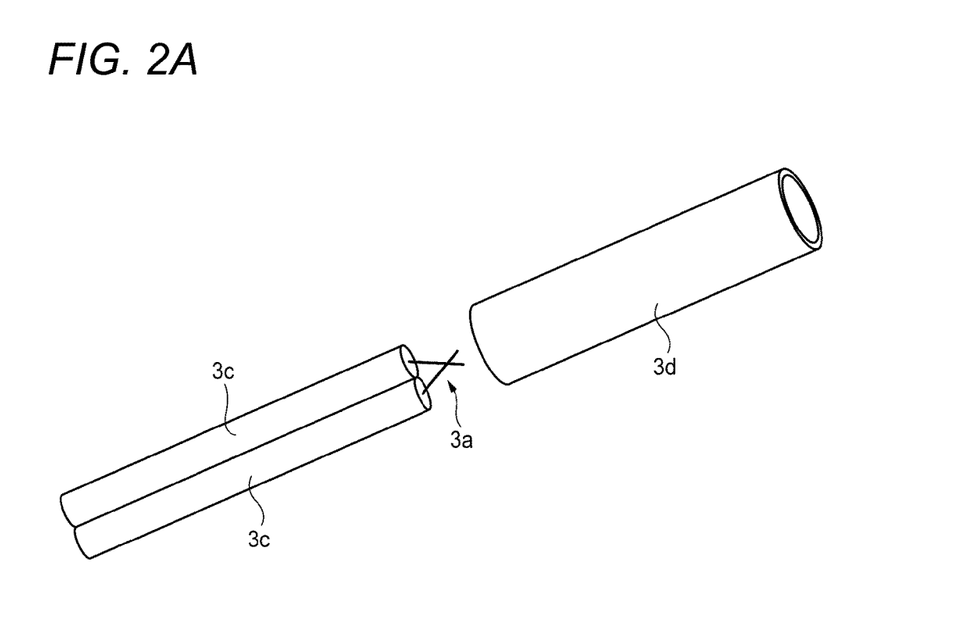
FIGS. 2A and 2B are views illustrating a method of producing the temperature sensor.

As shown in FIG. 2A, first, a pair of wire members 3c each including a metal wire are prepared, and the metal wires are joined together to form the heat sensitive portion 3a.

Figure 2B:
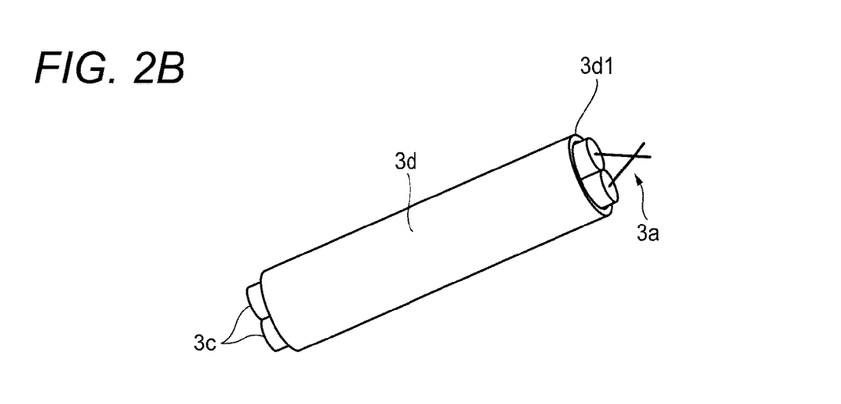

As shown in FIG. 2B, next, the pair of wire members 3c are bundled by a thin cylindrical member 3d. The cylindrical member 3d is made of an olefinic elastomer. Examples of an olefinic elastomer are polypropylene and ethylene-propylene rubber. At this time, the bundling is performed so that the heat sensitive portion 3a is exposed from the tip end edge 3d1 of the cylindrical member 3d.

Figure 3A:
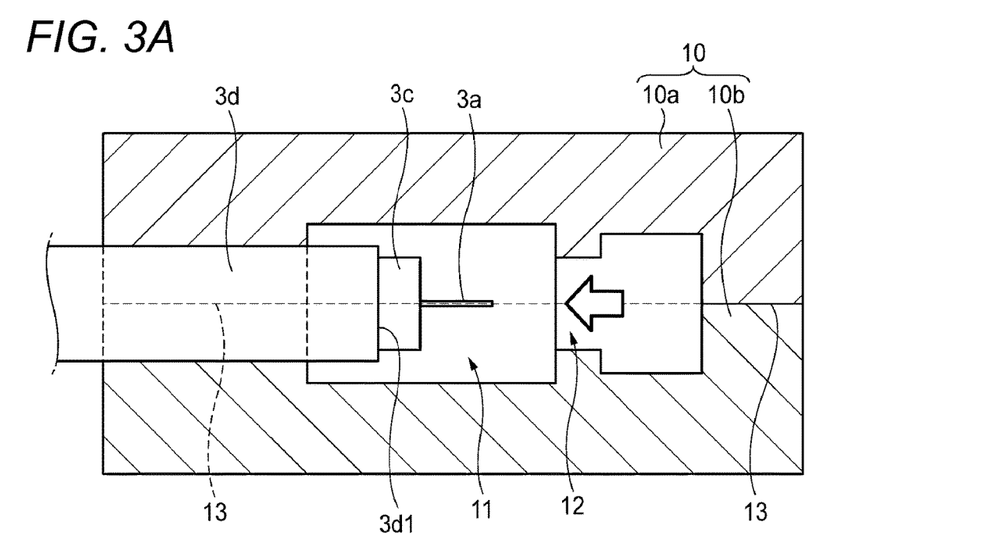
FIGS. 3A to 3C are views illustrating the method of producing the temperature sensor.

As shown in FIG. 3A, next, the thus formed heat sensitive portion 3a is placed in a cavity 11 of a mold 10.

Figure 4:
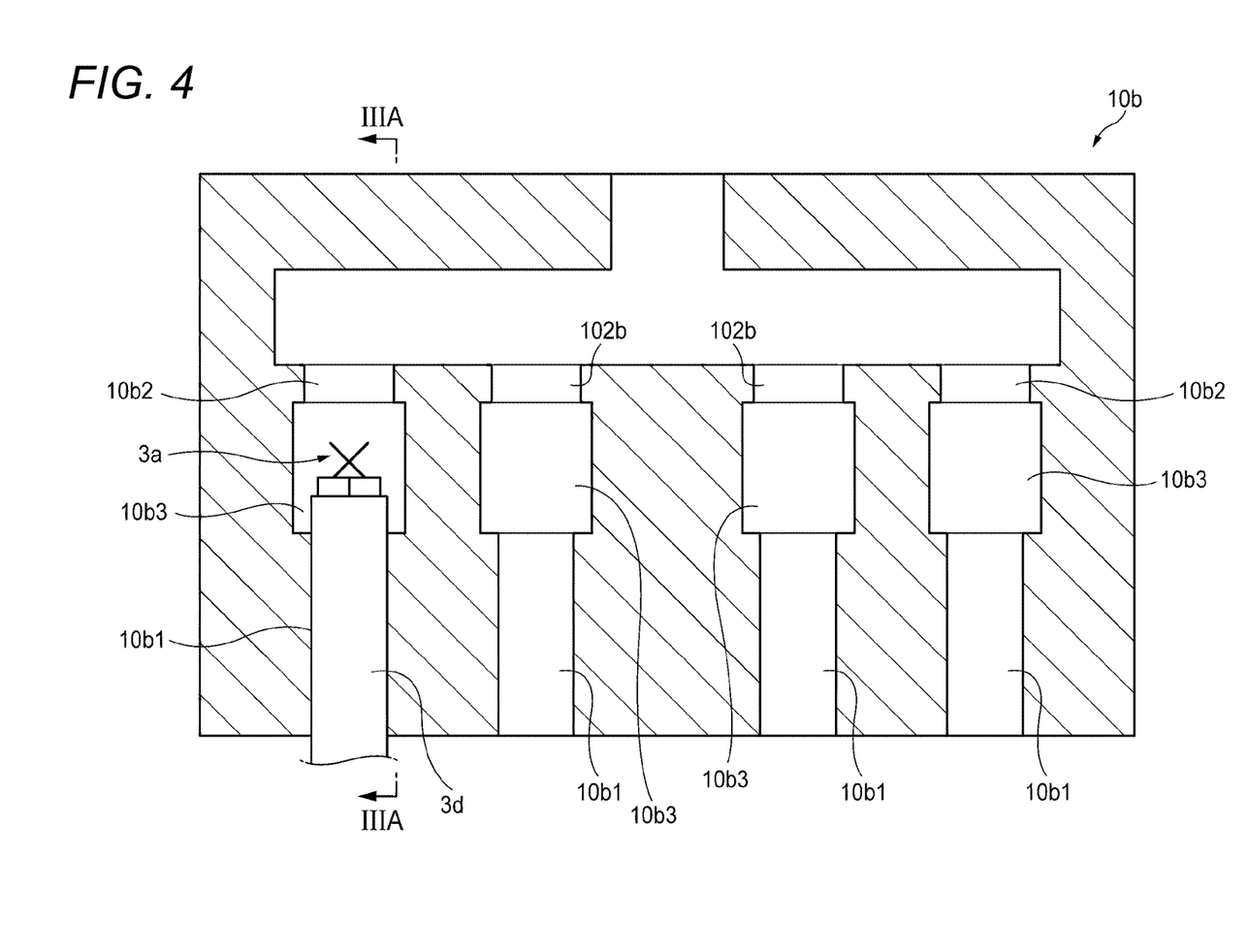
FIG. 4 is a view showing a part of a mold for producing the temperature sensor.

Specifically, the mold 10 includes an upper mold 10a and a lower mold 10b. FIG. 4 is a plan view of the lower mold 10b as seen from the upper side. FIG. 3A is a sectional view taken along line IIIA-IIIA in FIG. 4. In the lower mold 10b, a plurality of first grooves 10b1, a plurality of second grooves 10b2, and a plurality of recesses 10b3 are formed. The upper mold 10a has a similar structure. Namely, the mold 10 is configured so as to be able to collectively produce a plurality of heat sensitive elements 3.

Parts of the cylindrical members 3d each of which bundles the plurality of wire members 3c are placed in the first grooves 10b1, respectively. The heat sensitive portions 3a are placed in the recesses 10b3, respectively. Although FIG. 4 shows a state where the cylindrical member 3d and the heat sensitive portion 3a are placed in the first groove 10b1 and recess 10b3 which are located on the leftmost side, similar placement is performed also in the other first grooves 10b1 and recesses 10b3.

When the upper mold 10a and the lower mold 10b are coupled to each other in this state, cavities 11 and gates 12 are defined as shown in FIG. 3A. Specifically, the recesses 10b3 formed in the lower mold 10b, and the corresponding structure of the upper mold 10a define the cavities 11, and the second grooves 10b2 formed in the lower mold 10b, and the corresponding structure of the upper mold 10a define the gates 12. The reference numeral 13 denotes a parting surface which is formed by the coupling of the upper mold 10a and the lower mold 10b.

Next, a resin material is injected into the cavity through the gate 12 as shown by the arrow in FIG. 3A. An example of the resin material is an olefinic elastomer. Examples of an olefinic elastomer are polypropylene and ethylene-propylene rubber. As a result, the protective portion 3b which covers the heat sensitive portion 3a is molded.

Figure 3B:
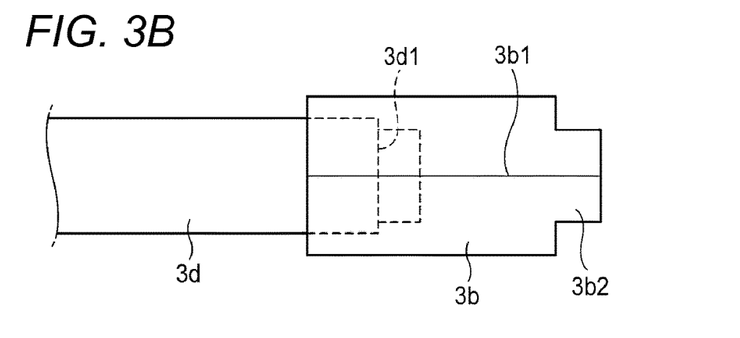

FIG. 3B shows a state where the tip end portion of the heat sensitive element 3 in which the protective portion 3b is formed is separated from the mold 10. A line trace 3b1 which is a trace caused by the parting surface 13 is formed on the outer surface of the protective portion 3b. The line trace 3b1 may be evidence of the execution of the production method of the embodiment.

Figure 3C:
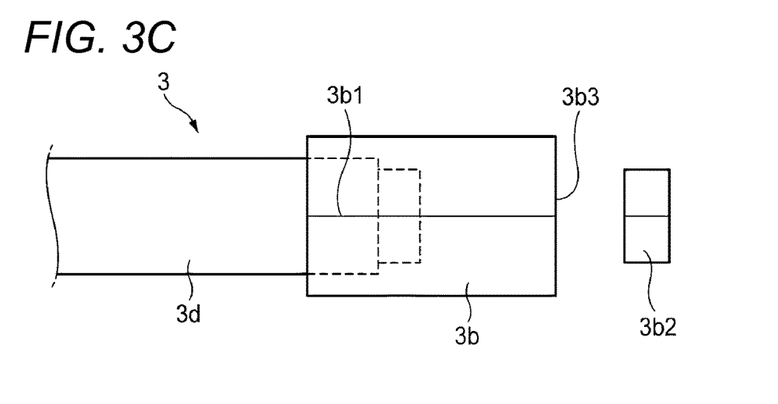

Moreover, a projection 3b2 which is a trace caused by the gate 12 is formed in the tip end of the protective portion 3b. As shown in FIG. 3C, next, the projection 3b2 is removed by cutting. As a result, the heat sensitive element 3 in the state shown in FIG. 1B is obtained. The thus produced heat sensitive elements 3 are attached to the body unit 2 of the temperature sensor 1 as shown in FIG. 1A.

In the case where the protective portion is to be formed by dipping, a resin is exposed to the external environment until the resin solidifies. Therefore, the resin is easily affected by the external environment, and, in solidification, it is difficult to keep constant the thickness of the resin among products. When the thickness of the resin is varied, there arises a case where the temperature detection characteristics of the heat sensitive portion covered by the resin are affected, and the characteristics of the sensor are changed. The inventors of the presently disclosed subject matter has found that this fact impedes improvement of the yield to contribute to reduction in production efficiency and increase in production cost. The inventors of the presently disclosed subject matter has repeatedly studied a technique which can be used in the formation of the protective portion 3b in place of the related-art dipping method. As a result, the inventors have found that employment of injection molding can solve all the problems.

When the protective portion 3b is molded by injection molding, the outer edge of the protective portion 3b is uniquely determined according to the shape of the cavity 11 of the mold 10 used in the injection molding. The injected resin is isolated in the cavity 11 from the external environment until the resin solidifies. Therefore, the configuration where the thickness of the protective portion 3b covering the heat sensitive portion 3a is kept constant among products can be easily realized. The thickness of the protective portion 3b can be easily controlled. Consequently, a plurality of temperature sensors in which the yield can be improved, and which have constant characteristics can be produced efficiently, at a low cost, and stably.

In the mold 10, the position of the gate 12 may be suitably determined. In the embodiment, as shown in FIG. 3A, the gate 12 is disposed at a position opposed to a tip end portion in the longitudinal direction of the heat sensitive element 3. Therefore, the resin material is injected into the cavity 11 along the longitudinal direction of the heat sensitive element 3.

According to the technique, the movement resistance of the resin can be evenly suppressed so that the resin surrounds the heat sensitive portion 3a, and the uniform protective portion 3b can be easily formed. Particularly, it is possible to suppress a phenomenon in which the flowing resin causes the thin metal wires that form the heat sensitive portion 3a, to be displaced in a direction perpendicular to the longitudinal direction of the heat sensitive element 3. Therefore, it is possible to suppress the direction dependence of the thickness of the resin of the protective portion 3b surrounding the heat sensitive element 3. Consequently, a plurality of temperature sensors having constant characteristics can be produced efficiently, at a low cost, and stably.

In the configuration where the gate 12 is placed as described above, as shown in FIG. 3B, the projection 3b2 which is a trace caused by the gate 12 is formed in the tip end of the protective portion 3b in the longitudinal direction of the heat sensitive element 3. When the projection 3b2 is cut off, as shown in FIG. 3C, a cut trace 3b3 is formed in the tip end of the protective portion 3b in the longitudinal direction of the heat sensitive elements 3. The cut trace 3b3 which is formed at this position may be evidence of the execution of the production method of the embodiment.

In the injection molding, as shown in FIG. 3A, the tip end edge 3d1 of the cylindrical member 3d is placed in the cavity 11. As shown in FIG. 3B, as a result, the tip end edge 3d1 of the cylindrical member 3d is covered by the molded protective portion 3b.

According to the technique, the resin which is injected into the cavity 11 enters the gap between the wire members 3c and the tip end edge 3d1 of the cylindrical member 3d, and, when the resin solidifies, the protective portion 3b, the wire members 3c, and the cylindrical member 3d can be firmly joined together. The wire members 3c can be firmly welded to each other. Therefore, the protective portion 3b can be prevented from slipping off during the use, and the property of protecting the heat sensitive portion 3a is enhanced. In the case where the gate 12 is disposed at a position opposed to the tip end edge 3d1 of the cylindrical member 3d as in the embodiment, particularly, the resin can be easily introduced into the gap between the tip end edge 3d1 and the wire members 3c. Therefore, a plurality of temperature sensors having constant characteristics can be produced efficiently, at a low cost, and stably.

The configuration of the mold for molding the protective portion 3b may be adequately determined. In the embodiment, as shown in FIG. 3A, the upper mold 10a and the lower mold 10b are configured so that, at least in a portion defining the cavity 11, the parting surface 13 extends in parallel to the longitudinal direction of the heat sensitive element 3. As shown in FIGS. 3B and 3C, as a result, the line trace 3b1 which is a trace of the parting surface 13 extends in a plane which is parallel to the longitudinal direction of the heat sensitive element 3, in the molded protective portion 3b.

According to the technique, while a plurality of heat sensitive elements 3 are juxtaposed in one (in the embodiment shown in FIG. 4, the lower mold 10b) of the pair of mold elements forming the parting surface 13, the protective portions 3b can be molded, and hence the working efficiency is improved. Therefore, a plurality of temperature sensors having constant characteristics can be produced efficiently, at a low cost, and stably.

Figure 5A:
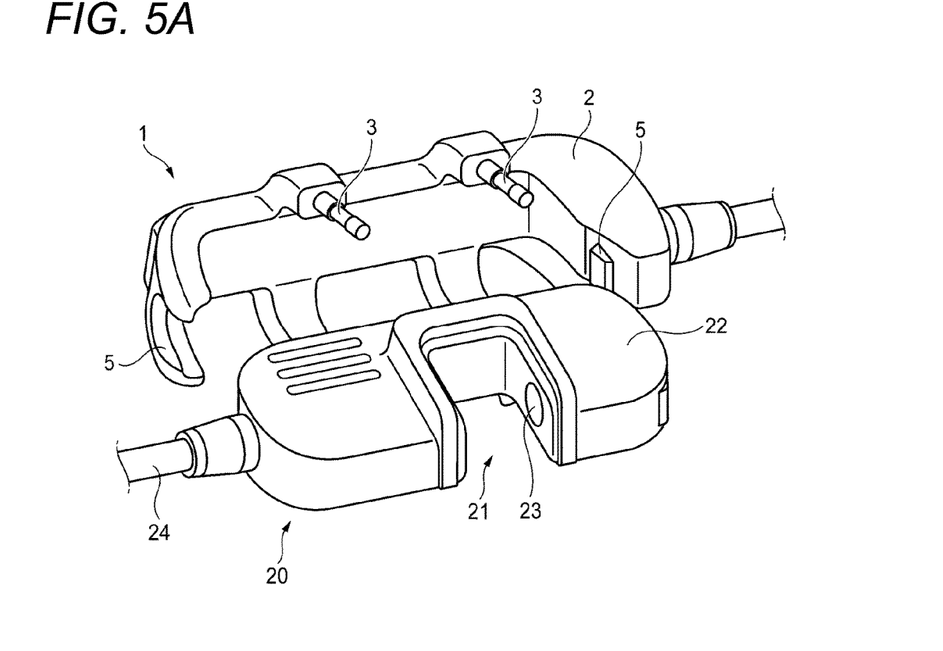
FIGS. 5A and 5B are views illustrating a manner of using the temperature sensor.
Figure 5B:
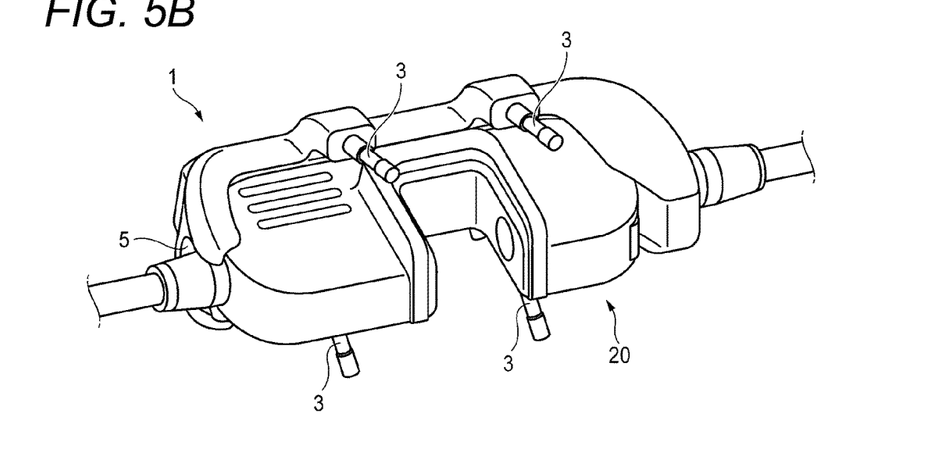
Figure 6:
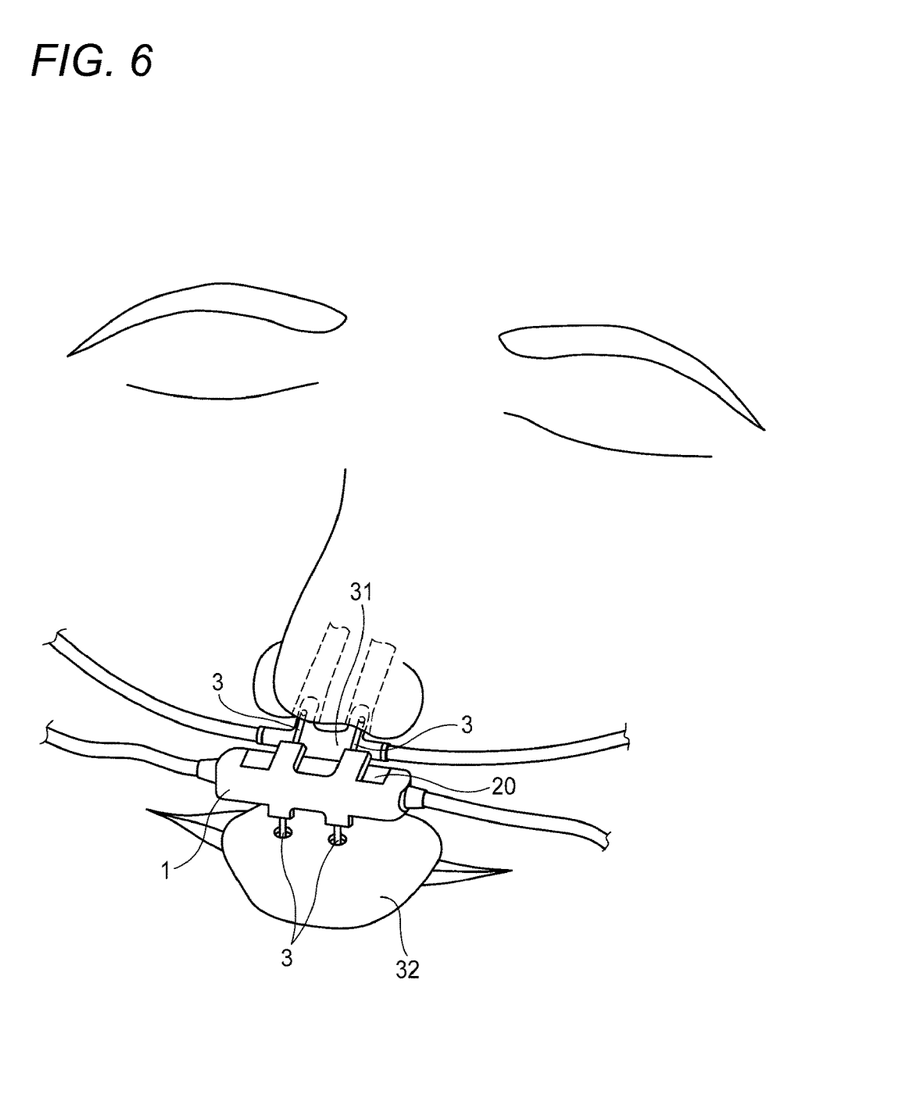
FIG. 6 is a view illustrating a manner of using the temperature sensor.

Referring to FIGS. 5A to 6, next, a manner of using the temperature sensor 1 which is produced by the above-described method will be described.

As shown in FIG. 5A, the temperature sensor 1 includes a plurality of connecting portions 5. The plurality of connecting portions 5 are configured so that, when the portions are engaged with a carbon dioxide concentration sensor 20, the temperature sensor 1 can be attached to the carbon dioxide concentration sensor 20. FIG. 5B shows a state where the temperature sensor 1 is attached to the carbon dioxide concentration sensor 20.

The carbon dioxide concentration sensor 20 includes the body unit 22 that defines a gas passage 21 through which the respiratory gas of the subject is to be passed. In the body unit 22, a light emitter and light receiver which are not shown are placed at positions which are opposed to each other across the gas passage 21, respectively. A pair of windows 23 (only one window is shown) through which light emitted from the light emitter and directed toward the light receiver can be passed are formed in wall portions which define the gas passage 21, and which are opposed to each other. As the wavelength of the light, a wavelength which is absorbed by carbon dioxide gas which is the detection target is selected. The intensity of the light incident on the light receiver is varied depending on the concentration of the carbon dioxide gas of the respiratory gas of the subject which is passed through the gas passage 21. A signal corresponding to the concentration is output through a cable 24.

As shown in FIG. 6, a first respiratory gas introducing portion 31 and a second respiratory gas introducing portion 32 can be attached to the carbon dioxide concentration sensor 20. The first respiratory gas introducing portion 31 is a member which efficiently guides the respiratory gas flowing through the nose of the subject, to the gas passage 21. The second respiratory gas introducing portion 32 is a member which efficiently guides the respiratory gas flowing through the mouth of the subject, to the gas passage 21. Namely, each of the first respiratory gas introducing portion 31 and the second respiratory gas introducing portion 32 includes a gas passage through which the respiratory gas of the subject is to be passed.

When the first respiratory gas introducing portion 31 and the second respiratory gas introducing portion 32 are attached to the concentration sensor, the plurality of heat sensitive elements 3 disposed in the temperature sensor 1 are placed in the respective gas passages of the first respiratory gas introducing portion 31 and the second respiratory gas introducing portion 32. The heat sensitive elements 3 placed in the gas passage of the first respiratory gas introducing portion 31 detect a temperature change of the respiratory gas flowing through the nose of the subject. The heat sensitive elements 3 placed in the gas passage of the second respiratory gas introducing portion 32 detect a temperature change of the respiratory gas flowing through the mouth of the subject.

The temperature sensor 1 may be configured so as to, in addition to or in place of the above-described connecting portions 5, include another connecting portion which can be attached to at least one of the first respiratory gas introducing portion 31 and the second respiratory gas introducing portion 32.

The foregoing description of the embodiment has been made in order to facilitate understanding of the invention, and is not intended to limit the invention. It is a matter of course that the invention may be changed or improved without departing the spirit thereof, and includes equivalents thereof.

The heat sensitive portion 3a is not limited to a junction of a pair of metal wires constituting a thermocouple. The heat sensitive portion 3a may be configured by either one of a thermistor and a resistance temperature detector. In this case, the cylindrical member 3d may be omitted.

At least one of the first respiratory gas introducing portion 31 and second respiratory gas introducing portion 32 which have been described with reference to FIG. 6 may be omitted in some cases.

According to the presently disclosed subject matter, there is provided a method of producing a temperature sensor which is configured to detect a temperature change of a respiratory gas of a subject, the method comprising: preparing a rod-like heat sensitive element which includes a heat sensitive portion in a tip end portion; placing the heat sensitive portion in a cavity of a mold; injecting a resin material into the cavity to mold a protective portion which covers the heat sensitive element; and releasing the tip end portion in which the protective portion is formed, from the mold.

Since the protective portion is molded by injection molding, the outer edge of the protective portion is uniquely determined according to the shape of the cavity of the mold used in the injection molding. The injected resin is isolated in the cavity from the external environment until the resin solidifies. Therefore, the configuration where the thickness of the protective portion covering the heat sensitive portion is kept constant among products can be easily realized. The thickness of the protective portion can be easily controlled. Consequently, a plurality of temperature sensors in which the yield can be improved, and which have constant characteristics can be produced efficiently, at a low cost, and stably.

Also a temperature sensor which is obtained by the production method is a mode provided by the presently disclosed subject matter. The temperature sensor includes: a rod-like heat sensitive element which includes a heat sensitive portion in a tip end portion; and a resin-made protective portion which covers the heat sensitive element, and in which a line trace is formed. The line trace is a trace caused by a parting surface which is formed by a pair of mold elements defining the cavity.

The heat sensitive portion may be one of a junction of a pair of metal wires constituting a thermocouple, a thermistor, and a resistance temperature detector. The resin material may be injected into the cavity along a longitudinal direction of the heat sensitive element.

According to the configuration, the movement resistance of the resin can be evenly suppressed so that the resin surrounds the heat sensitive portion, and a uniform protective portion can be easily formed. In the case where the heat sensitive portion is formed by a junction of a pair of metal wires constituting a thermocouple, particularly, it is possible to suppress a phenomenon in which the flowing resin causes the metal wires to be displaced in a direction perpendicular to the longitudinal direction of the heat sensitive element. Therefore, it is possible to suppress the direction dependence of the thickness of the resin of the protective portion surrounding the heat sensitive elements. Consequently, a plurality of temperature sensors having constant characteristics can be produced efficiently, at a low cost, and stably.

Also a temperature sensor which is obtained by the production method is a mode provided by the presently disclosed subject matter. Namely, a cut trace is formed in the tip end of the protective portion of the temperature sensor. In the case where the resin is injected into the cavity along the longitudinal direction of the heat sensitive element, a gate trace remains on the tip end of the molded protective portion. In a heat sensitive element which is a product, a trace which is formed by cutting off the gate trace remains.

The heat sensitive portion may include a plurality of wire members, and the heat sensitive element may include a cylindrical member which is configured to bundle the plurality of wire members. In this case, when the tip end portion is placed in the cavity, a tip end edge of the cylindrical member is placed in the cavity.

According to the configuration, the resin which is injected into the cavity enters the gap between the wire members and the tip end edge of the cylindrical member, and, when the resin solidifies, the protective portion, the wire members, and the cylindrical member can be firmly joined together. Therefore, the protective portion can be prevented from slipping off during the use, and the property of protecting the heat sensitive portion is enhanced. In the case where the resin is injected along the longitudinal direction of the heat sensitive element, particularly, the resin can be easily introduced into the gap between the wire members and the tip end edge. Therefore, a plurality of temperature sensors having constant characteristics can be produced efficiently, at a low cost, and stably.

Also a temperature sensor which is obtained by the production method is a mode provided by the presently disclosed subject matter. Namely, the tip end edge of the cylindrical member of the temperature sensor is covered by the protective portion.

In a portion defining the cavity, a parting surface of the mold may extend in parallel to a longitudinal direction of the heat sensitive element.

According to the configuration, the protective portion can be molded while a plurality of heat sensitive elements are juxtaposed in one of the pair of mold elements forming the parting surface, and hence the working efficiency is improved. Therefore, a plurality of temperature sensors having constant characteristics can be produced efficiently, at a low cost, and stably.

Also a temperature sensor which is obtained by the production method is a mode provided by the presently disclosed subject matter. Namely, the line trace in the temperature sensor extends in a plane which is parallel to the longitudinal direction of the heat sensitive element.

A temperature sensor which is obtained by the production method has a configuration where it includes a connecting portion that is attachable to a member having a gas passage through which the respiratory gas of the subject is to be passed.

What is claimed is:

1. A method of producing a temperature sensor which is configured to detect a temperature change of a respiratory gas of a subject, the method comprising:
   preparing a rod-like heat sensitive element which includes a heat sensitive portion in a tip end portion;
   placing the heat sensitive portion in a cavity of a mold;
   injecting a resin material into the cavity through a gate of the mold along a longitudinal direction of the heat sensitive element to mold a protective portion which covers the heat sensitive element;
   releasing the tip end portion in which the protective portion is formed, from the mold; and
   removing a projection which is a trace caused by the gate and which is formed in a tip end of the protective portion.

2. The method according to claim 1, wherein
   the heat sensitive portion is one of a junction of a pair of metal wires constituting a thermocouple, a thermistor, and a resistance temperature detector.

3. The method according to claim 1, wherein
   the heat sensitive portion includes a plurality of wire members, the heat sensitive element includes a cylindrical member which is configured to bundle the plurality of wire members, and,
   when the tip end portion is placed in the cavity, a tip end edge of the cylindrical member is placed in the cavity.

4. The method according to claim 1, wherein,
   in a portion defining the cavity, a parting surface of the mold extends in parallel to the longitudinal direction of the heat sensitive element.

5. The method according to claim 1, wherein
   the gate is disposed at a position opposed to the tip end portion in the longitudinal direction of the heat sensitive element.

6. A temperature sensor that is produced by the method according to claim 1 which is configured to detect a temperature change of a respiratory gas of a subject, the temperature sensor comprising:
   a rod-like heat sensitive element which includes a heat sensitive portion in a tip end portion; and
   a resin-made protective portion which covers the heat sensitive element, wherein
   a cut trace is formed in a tip end of the protective portion.

7. The temperature sensor according to claim 6, wherein the heat sensitive portion is one of a junction of a pair of metal wires constituting a thermocouple, a thermistor, and a resistance temperature detector.

8. The temperature sensor according to claim 7, wherein the heat sensitive portion includes a plurality of wire members, the rod-like heat sensitive element includes a cylindrical member which is configured to bundle the plurality of wire members, and a tip end edge of the cylindrical member is covered by the protective portion.

9. The temperature sensor according to claim 6, wherein a line trace is formed in the protective portion and extends in a plane which is parallel to a longitudinal direction of the heat sensitive element.

10. The temperature sensor according to claim 6, wherein the sensor includes a connecting portion that is attachable to a member including a gas passage through which the respiratory gas of the subject is to be passed.

11. A temperature sensor which is produced by the method according to claim 1, wherein a line trace is formed in the protective portion, and a cut trace is formed in a tip end of the protective portion.

* * * * *